United States Patent [19]

Bollag et al.

[11] 3,931,268

[45] Jan. 6, 1976

[54] METHYLHYDRAZINOMETHYL-SUBSTITUTED BENZOIC ACID AMIDES

[75] Inventors: Werner Bollag, Basel; Hugo Gutmann, Reinach; Balthasar Hegedüs, Binningen; Ado Kaiser, Neu-Frenkendorf; Albert Langemann, Binningen; Marcel Müller, Frenkendorf; Paul Zeller, Allschwil, all of Switzerland

[73] Assignee: Hoffmann-La Roche Inc., Nutley, N.J.

[22] Filed: May 6, 1970

[21] Appl. No.: 35,292

Related U.S. Application Data

[60] Division of Ser. No. 593,734, Nov. 14, 1966, Pat. No. 3,520,926, which is a continuation-in-part of Ser. No. 200,059, June 5, 1962, abandoned.

[30] Foreign Application Priority Data

June 9, 1961 Switzerland.......................... 6734/61

[52] U.S. Cl.......... 260/465 D; 260/558 H; 260/490
[51] Int. Cl.²................C07C 103/76, C07C 103/78; C07C 103/82; C07C 103/22
[58] Field of Search................. 260/558 H, 465, 490

[56] References Cited
UNITED STATES PATENTS
3,520,926    7/1970    Bollag................................ 260/558

*Primary Examiner*—Harry I. Moatz
*Attorney, Agent, or Firm*—Samuel L. Welt; Bernard S. Leon; William G. Isgro

[57] ABSTRACT

Benzene-ring substituted (2-methylhydrazino)methylbenzene compounds and intermediates therefor are described. The former compounds are useful as cytostatic agents.

8 Claims, No Drawings

METHYLHYDRAZINOMETHYL-SUBSTITUTED BENZOIC ACID AMIDES

CROSS-REFERENCE TO RELATED APPLICATIONS

This application is a division of application Ser. No. 593,734, filed Nov. 14, 1966, now U.S. Pat. No. 3,520,926, issued July 21, 1970, which in turn is a continuation in part of Ser. No. 200,059, filed June 5, 1962, now abandoned.

DETAILED DESCRIPTION OF THE INVENTION

This application relates to novel hydrazine compounds useful as cytostatic agents. More particularly, the novel compounds in this invention are selected from the group consisting of compounds of the formula

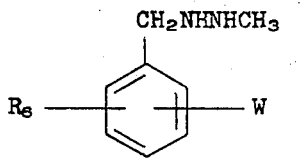

and pharmaceutically acceptable acid addition salts thereof;

wherein W is selected from the group consisting of

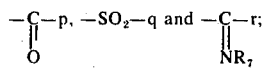

$R_6$ is selected from the group consisting of hydrogen and halogen; $R_7$ is selected from the group consisting of hydrogen and lower alkyl; $p$ is selected from the group consisting of hydrogen, lower alkyl and

$q$ is selected from the group consisting of lower alkyl and

$r$ is

and $R_4$ and $R_5$ are each selected from the group consisting of, taken separately, hydroxy-lower alkyl, lower alkanoyloxy-lower alkyl, lower alkylamino-lower alkyl, di-lower alkylamino-lower alkyl, (2-methylhydrazinomethyl)-phenyl, phenyl-lower alkyl, hydrogen, lower alkoxy-lower alkyl, lower alkylthio-lower alkyl, lower alkylsulfonyl-lower alkyl, pyridylmethyl, furfuryl, tetrahydrofurfuryl, lower alkyl, lower alkenyl, cyclo-lower alkyl, carbamoyl, lower alkylcarbamoyl, cyano-lower alkyl, halo-lower alkyl and halo-hydroxy-lower alkyl and, taken together, lower alkylene and lower alkyleneoxy-lower alkylene of 4 to 5 atom chain length.

Exemplary of the various phenyl ring substituents comprehended by W in the formula I are the following:

amidino groups, the hydrogen atoms of which can be in part or completely replaced by saturated or unsaturated aliphatic, cycloaliphatic, araliphatic, aromatic or heterocyclic radicals which themselves can bear further functional groups, for example, methylamidino, diisopropylamidino, cyclopropylamidino, phenylamidino, benzylamidino, isoxazolylamidino and (hydroxyethyl)amidino;

carbamoyl groups, the hydrogen atoms of which can be replaced by saturated or unsaturated aliphatic or alicyclic radicals which themselves can bear further functional groups or aromatic or heterocyclic radicals, for example, mono and dialkylcarbamoyl such as N-methylcarbamoyl, N,N-dimethylcarbamoyl, N-isopropylcarbamoyl, N-isobutylcarbamoyl, N-tert.-butylcarbanoyl, N,N-diisopropylcarbamoyl, N-tert.-amylcarbamoyl, N-tert.-octylcarbamoyl; as well as N-alkoxyalkylcarbamoyl groups such as methoxyethylcarbamoyl; N-hydroxyalkylcarbamoyl, such as hydroxyethylcarbamoyl; N-alkylthioalkylcarbamoyl groups such as methylthioethylcarbamoyl; N-carbamoyl-alkylcarbamoyl groups such as carbamoyl, methylcarbamoyl; N-alkylsulfonylalkylcarbamoyl groups such as methylsulfonylethylcarbamoyl; N-haloalkylcarbamoyl groups such as β-chloroethylcarbamoyl and β, β, β-trifluoroethylcarbamoyl; N-alkenylcarbamoyl groups such as N-allylcarbamoyl; N-aralkylcarbamoyl groups such as benzylcarbamoyl; N-furfurylcarbamoyl; N-cycloalkylcarbamoyl groups such as N-cyclopropylcarbamoyl; N-alkylaminoalkylcarbamoyl and N-dialkylaminoalkylcarbamoyl groups such as β-methylaminoethylcarbamoyl and diethylaminoethylcarbamoyl: and N,N-alkylenecarbamoyl groups such as N,N-tetramethylenecarbamoyl and N,N-pentamethylenecarbamoyl;

allophanoyl groups, the hydrogen atoms of which can be in part or completely replaced by saturated or unsaturated aliphatic, cycloaliphatic, araliphatic, aromatic or heterocyclic radicals which themselves can bear further functional groups, for example, 4-methylallophanoyl, 2-isopropylallophanoyl;

sulfamoyl groups, the hydrogen atoms of which can be substituted by alkyl groups such as lower alkyl groups, for example, N,N-dimethylsulfamoyl;

lower alkylsulfonyl groups, for example methylsulfonyl;

acyl radicals of lower aliphatic carboxylic acid, for example, formyl, acetyl and propionyl, and of aromatic carboxylic acids, for example, benzoyl.

A preferred subgenus of compounds of formula I are benzamides, i.e., those compounds of formula I wherein W is

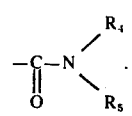

Another preferred subgenus of formula I are those compounds of formula I wherein $R_6$ is hydrogen. An especially preferred subgenus of compounds of formula I are those methylhydrazinomethyl benzamides of the formula

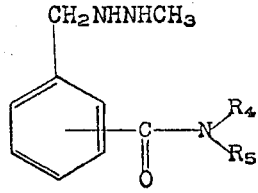

II and pharmaceutically acceptable acid addition salts thereof wherein $R_4$ and $R_5$ have the same meaning as above. An especially preferred subgenus of compounds of formula II are those compounds, as well as pharmaceutically acceptable acid accition salts thereof, wherein $R_4$ and $R_5$ are each selected from the group consisting of, taken separately, hydroxy-lower alkyl, hydrogen, lower alkoxy-lower alkyl, lower alkyl, cyclo-lower alkyl, carbamoyl, cyano-lower alkyl, halo-lower alkyl and, taken together, lower alkylene of 4–5 carbon atoms. Of this subgenera, particularly valuable compounds are [(2-methylhydrazino)-methyl]benzamides and N-lower alkyl-[(2-methylhydrazino)-methyl]benzamides.

The compounds of formula I can be prepared by aralkylation of a compound of the formula $$CH_3-NH-NH_2 \quad \text{III}$$

wherein the hydrogen atoms of the hydrazine group may partially be substituted by protecting groups such as acyl, carbalkoxy, carbobenzoxy of benzyl, with a compound yielding the moiety $$X'-C_6H_4-CH_2 \quad \text{IV}$$

wherein X' has the same meaning as W or is a substituent convertible into a substituent represented by W in formula I;
or by methylation of a compound of the formula $$X'-C_6H_4-CH_2-NH-NH_2 \quad \text{V}$$

wherein X' has the same meaning as indicated above and the hydrogen atoms of the hydrazine group may partially be substituted by protecting groups such as acyl, carbalkoxy, carbobenzoxy or benzyl; if necessary converting the moiety X' in the resulting hydrazine into a moiety represented by W; if necessary splitting off such protecting groups as are present; and if desired converting the so-obtained product of formula I into a salt.

One embodiment of the invention consists of aralkylating methylhydrazine or a methylhydrazine, the nitrogen atoms of which are partially substituted by protecting groups, with an agent yielding the residue $X'-C_6H_4-CH_2-$. This aralkylation can be effected, for example, by use of the following aralkylating agents: 4-carbamoylbenzyl bromide, 4-cyanobenzyl bromide, 4-carbalkoxybenzyl bromide, 2-cyanobenzyl bromide, 4-carbamoyl-2-chlorobenzyl bromide, 4-benzoylbenzyl bromide, 4-acetylbenzyl bromide, and the like. When using a dihalo compound as an aralkylating agent it is convenient to use two moles of methylhydrazine, thereby forming compounds bearing two methylhydrazino groups.

It is suitable in order to effect aralkylation to first convert the hydrazine compound of formula III above into a salt, preferably via treatment with an alkali metal alcoholate in an alcoholic solution. After removal of the alcohol, the resulting salt is advantageously dissolved in an inert solvent, for example, dimethylformamide, and treated with an aralkylating agent, preferably at an elevated temperature. The reaction product can be purified by conventional methods, for example, via extraction, crystallization or distillation.

The introduction of the aralkyl moiety can also be effected by a reaction of methylhydrazine or methylhydrazine partially substituted by protecting groups, for example, 1-methyl-1-acetylhydrazine with a carbonyl compound, followed by reduction of the so-formed hydrazone, as well as eventual splitting off of the protecting groups. This reaction can suitably be effected via a short heating of the reaction components in a solvent, such as, for example, alcohol, and reduction of the resulting hydrazone in the presence of a hydrogenation catalyst, such as palladium or platinum.

According to a further variation of the reaction, there is aralkylated with an agent yielding the moiety $X'-C_6H_4-CH_2-$ a compound of the formulae

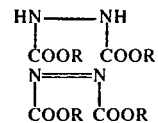

wherein R represents lower alkyl, which has been methylated.

Following the aralkylation, the carbalkoxy substituents are split off. The aralkylation can be undertaken in the same manner as previously described.

According to another embodiment of the invention, hydrazine compounds of formula V are methylated. This methylation can be conducted, for example, with the help of a methylating agent, such as, methyliodide or dimethylsulphate, under the conditions previously described for the aralkylation reaction.

The introduction of the methyl group can also be effected via reaction of a compound of formula V above with formaldehyde, followed by reduction of the condensation product. Condensation is suitably effected with equimolar amounts of the hydrazine of formula V and of the formaldehyde. The hydrogenation of the condensation product can proceed simultaneously with the condensation reaction or subsequent thereto. Advantageously, it is conducted in the presence of a hydrogenation catalyst, such as platinum or palladium, until the absorption of an equimolar amount of hydrogen. The working up of the reaction mixture can be effected by conventional means, for example, via fractional distillation.

Products of formula I above can also be obtained via methylation of a product obtained via aralkylation of a compound of formulae VI or VII above.

Any protecting groups present in the reaction products can be split off according to known procedures.

The reaction products formed by the above-outlined processes can, if desired, be additionally substituted in the phenyl ring. Thus, for example, compounds of formula I above, the hydrazine group of which is provided with protecting groups such as those previously described, can be nitrated, for example, via treatment with potassium nitrate in concentrated sulfuric acid at a temperature of from about 0°C. to about 70°C. Via reaction with chlorine or bromine in the presence of a suitable catalyst, for example, ferric chloride, at slightly elevated temperatures, halogen atoms can be introduced as substituents on the benzene nucleus.

Where necessary, the conversion of the moiety $X'—C_6H_4$ into the moiety $W—C_6H_4$ can be effected in the above-described reaction procedures at any point of time. Thus, it is advantageous, for example, to prepare substituted carbamoyl compounds from 4-[(2-methyl-1,2-dicarbobenzoxy-hydrazino)-methyl]-benzoic acid, itself obtained by a saponification of corresponding methyl or ethylesters, via reaction with amines in accord with known methods of amidation. Suitably, the acid is converted into a reactive derivative, for example, into an acid chloride or a mixed anhydride, for example, with a carbonic acid monoester or into an activated ester, for example, a cyanomethylester. The acid can also be amidated directly via use of a condensation agent such as dicyclohexylcarbodiimide. The above-mentioned amides can also be obtained in the presence of a strong acid from [(2-methyl-1,2-dicarbobenzoxy-hydrazino)-methyl]-benzonitrile via reaction with olefins, for example, isobutylene or secondary or tertiary alcohols. Hydrolysis of the nitriles by means of strong acids or with hydrogen peroxide and alkalis produces N-unsubstituted benzamides. Protecting groups are subsequently removed from carbamoyl compounds obtained according to this method via hydrogenolysis or treatment with a hydrogen bromide/glacial acetic acid solution. The resulting hydrobromides obtained by the latter method can, if desired, be converted into corresponding free bases and/or into other salts.

Amidino or substituted amidino compounds of formula I are advantageously prepared from methylhydrazinomethyl-benzonitriles, the hydrazine group of which is substituted by protecting groups, via the corresponding imido ether, which can be obtained via reaction of the nitrile with alcohol and mineral acid. By reaction of the imido ether with ammonia or a primary or secondary amine, the desired amidino compound is obtained. Suitably protected methylhydrazinomethyl-benzonitriles can also be reacted directly with the salts of amines, for example, isopropylamine hydrochloride or isopropylamine tosylate at elevated temperatures, and the desired products of formula I can be obtained via subsequent removal of the protecting groups. One further method consists of converting a mono-substituted methylhydrazinomethyl-benzamide, the hydrazine groups of which are substituted by protecting groups, for example, 4-[(2-methyl-1,2-dicarbobenzoxyhydrazino)-methyl]-benzoic acid isopropylamide, via reaction with a phosphorus halide, for example, phosphorus pentachloride, into corresponding imido halides, which then, in turn, can be reacted with ammonia, primary, or secondary amines, whereby there is obtained upon removal of the protecting groups, amidines and mono- or disubstituted amidines.

The substituted aromatic hydrazine compounds of formula I form pharmaceutically acceptable acid addition salts with both pharmaceutically acceptable inorganic and organic acids, such as, for example, hydrohalic acids, as hydrogen chloride, hydrogen bromide, hydrogen iodide, as well as other mineral acids, such as sulfuric acid, phpsphoric acid, nitric acid, and with organic acids, such as tartaric acid, citric acid, oxalic acid, camphorsulfonic acid, ethanesulfonic acid, toluenesulfonic acid, salicylic acid, ascorbic acid, maleic acid, mandelic acid, and the like. Preferred salts are the hydrohalides, especially the hydrochloride. The acid addition salts can suitably be prepared via treatment of the hydrazine derivative in an inert solvent with the corresponding acid.

The compounds of formula I are active cytostatic agents. They inhibit the growth of transplantable tumors in both mice and rats. Thus, they are active, for example, against Walker tumors, Erlich carcinoma, Erlich ascites carcinoma, and the like. Also these compounds cause decomposition of macromolecular desoxyribonucleic acid in solution. The compounds can be administered internally in the form of conventional pharmaceutical preparations, for example, the bases of formula I or their pharmaceutically acceptable acid addition salts can be administered in conventional enteral or parenteral pharmaceutical excipients containing organic and/or inorganic inert carriers, such as water, gelatin, lactose, starch, magnesium stearate, talc, plant oils, gums, alcohol, Vaseline, or the like. The pharmaceutical preparations can be in conventional solid forms, for example, tablets, dragees, suppositories, capsules, or the like, or conventional liquid forms, such as suspensions, emulsions, or the like. If desired, they can be sterilized and/or contain conventional pharmaceutical adjuvants, such as, preservatives, stabilizing agents, wetting agents, emulsifying agents, buffers, or salts used for the adjustment of osmotic pressure. The pharmaceutical preparations can also contain other therapeutically active materials.

It is to be understood that when the moiety "$X'—C_6H_4$" is used in the discussion above, there is comprehended the moiety

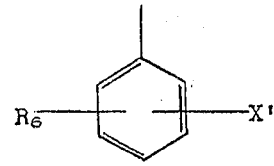

in analogy to the moiety

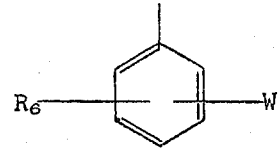

shown in formula I above.

The following examples are illustrative, but not limitative of the invention. All temperatures are in degrees Centigrade.

EXAMPLE 1

24.7 g. of 1-methyl-1,2-diacetyl-hydrazine were added to a solution of 4.38 g. of sodium in 150 ml. of absolute ethanol and 27.5 g. of 2-cyano-benzyl chloride were then added to the resulting mixture, which was then heated under reflux for 4 hours. The precipitated salt was filtered off and the filtrate concentrated in vacuo. The residue was treated with water and extracted over 15 hours with a mixture of ether and methylene chloride (2:1). Concentration of the extract yielded a residue that was heated under a nitrogen atmosphere for 2 hours with a mixture of 85 ml. of concentrated hydrochloric acid and 67 ml. of water. The reaction solution was then concentrated and rendered alkaline by addition of sodium hydroxide, whereupon 2[(2-methyl-hydrazino)-methyl]-benzamide separated out. The dihydrobromide prepared therefrom was crystallized from glacial acetic acid and melted at 240°–242°.

EXAMPLE 2

First, 2.05 g. of sodium and then 28 g. of 1-methyl-1,2-dicarbobenzoxy-hydrazine were dissolved in 150 ml. of absolute ethanol, and the solution was evaporated to dryness under reduced pressure. The residue was dissolved in 100 ml. of dimethylformamide, and to this solution were added at one time with stirring 20.5 g. of 4-(bromomethyl)-benzamide. The reaction was exothermic and the temperature of the reaction mixture rose to about 60°. The reaction mixture was stirred for 2 hours, then poured into 500 ml. of water and extracted 3 times with ether/methylene chloride (3:1). The organic extracts were washed 5 times with water, dried with sodium sulfate and evaporated to dryness in vacuo. The residual oil was dissolved in 180 ml. of a 33% solution of hydrogen bromide in glacial acetic acid, and the resulting solution permitted to stand for 4 hours at room temperature. The crystals that separated were filtered off, washed with glacial acetic acid and ether, and recrystallized from ethanol, yielding 4-[(2-methyl-hydrazino)-methyl]-benzamide hydrobromide, melting at 173°–175°.

In an analogous manner, the following compounds were prepared:

3-[(2-methyl-hydrazino)-methyl]-benzamide hydrobromide, melting at 142°–143°,

4-[(2-methyl-hydrazino)-methyl]-benzoic acid methylamide hydrobromide, melting at 186°–187°, 4-[(2-methyl-hydrazino)-methyl]-benzenesulfonic acid dimethylamide dihydrobromide, melting at 126°–128°, 4-[(2-methyl-hydrazino)-methyl]-3-chloro-benzamide hydrobromide, melting at 197°–199°.

EXAMPLE 3

15 g. of 4-[(2-methyl-1,2-dicarbobenzoxyhydrazino)methyl]-benzoic acid were boiled with an excess of thionyl chloride for 1 hour under reflux. The unconverted thionyl chloride was distilled off in vacuo, the residue twice dissolved each time in 75 ml. of absolute benzene and then concentrated in vacuo. The so-obtained 4-[(2-methyl-1,2-dicarbobenzoxyhydrazino)-methyl]-benzoyl chloride, a viscous light yellow oil, was dissolved in 50 ml. of absolute benzene and with stirring mixed with a solution of 4.45 g. of isopropylamine in 100 ml. of absolute benzene. By cooling, the temperature of the reaction mixture was kept below 30°. After the mixing had been completed, the reaction mixture was maintained first at room temperature for 3 hours and then for ½ hour at 40°. It was then cooled down and poured into about 100 ml. of ice water. After the addition of a mixture of methylene chloride and ether (40 ml. + 200 ml.), the organic phase was separated and then washed with water, dilute hydrochloric acid, water, dilute sodium hydroxide and again with water. The solvents were then evaporated, yielding 4-[(2-methyl-1,2-dicarbobenzoxyhydrazino)-methyl]-benzoic acid isopropylamide as a yellow oil, which crystallized upon triturating with ether; m.p. 90°–92°. This product was then covered with 70 ml. of a 33 % solution of hydrogen bromide in glacial acetic acid, and then permitted to stand for 2 hours with occasional swirling, whereupon a thick slurry of crystals was formed. The precipitate was filtered off, washed with 20 ml. of glacial acetic acid and finally with ether, yielding crystals of 4-[(2-methyl-hydrazino)-methyl]-benzoic acid isopropylamide hydrobromide, which after recrystallization from methanol/ether melted at 216°–217° (dec.).

The above-mentioned acid starting material was prepared as follows:

544 g. of 4-methyl-benzoic acid was boiled with 550 ml. of thionyl chloride until a clear solution was obtained. After the excess thionyl chloride was distilled off, the residue was fractionated, yielding 605 g. of 4-methyl-benzoyl chloride; b.p. 91°/9 mm Hg., $n_D^{24}$ = 1.5532. This was dissolved in 550 ml. of absolute benzene and the so-formed solution added to a mixture of 248 ml. of absolute methanol and 550 ml. of absolute benzene. After the exothermic reaction had terminated, the reaction mixture was boiled for a further 20 hours, then concentrated in vacuo and the product, 4-methyl-benzoic acid methyl ester, isolated by conventional means. It could be purified by distillation, and the purified product boiled at 91°/9 mm Hg., m.p. 32°.

574 g. of this ester were dissolved in 1200 ml. of carbontetrachloride and, while boiling and exposing to a U.V. lamp, treated dropwise with a solution of 109 ml. of bromine in 400 ml. of carbontetrachloride. After all of the bromine had been dropped in, the mixture was heated for a further hour, concentrated in vacuo and the residue crystallized from low boiling petroleum ether, yielding as colorless fine crystals, 4-(bromomethyl)benzoic acid methyl ester, which melted at 52°. For the reaction of this ester with 1-methyl-1,2-dicarbobenzoxy-hydrazine, the following procedure was followed:

309 g. of a 27% suspension of sodium hydride in an inert solvent were treated with 300 ml. of dimethylformamide, and a solution of 1095 g. of 1-methyl-1,2-dicarbobenzoxy-hydrazine in dimethylformamide was added thereto. When all the material had been added and the hydrogen evolution had nearly come to a standstill, the mixture was heated for an hour at about 80° in order to carry the formation of the sodium salt to completion. A mixture of 759 g. of 4-(bromo-methyl)-benzoic acid methyl ester in 700 ml. of dimethylformamide was then dropped in, and finally the reaction mixture was heated for an hour at 80°. After cooling, the reaction mixture was poured into 10 liters of ice water and the condensation products taken up in ether. The thereby obtained crude methyl ester ($n_D^{24}$ = 1.1558) was used without further purification for the next step. It was dissolved in about 2200 ml. of dioxane, treated with a solution of 133 g. of sodium hydroxide in 870 ml. of water, and the resulting mixture stirred for about 24 hours at room temperature. It was then poured into about 10 liters of ice water and neutral materials were extracted with ether. The aqueous phase was rendered acid with concentrated hydrochloric acid (weak congo red) and the separated acid taken up in ether. The isolated crude acid was recrystallized from dibutyl ether, yielding colorless crystals of 4-[(2-methyl-1,2-dicarbobenzoxy-hydrazino)-methyl]-benzoic acid, which melted at 112°. The so-obtained product was sufficiently pure for further reaction.

In a similar way, but using different amines, the following compounds were prepared:

4-[(2-methyl-hydrazino)-methyl]-benzoic acid methylamide hydrobromide, m.p. 186°–187°, 4-[(2-methyl-hydrazino)-methyl]-benzoic acid ethylamide hydrobromide, m.p. 164°–165°, 4-[(2-methyl-hydrazino)-methyl]-benzoic acid n-propylamide hydrobromide, m.p. 177°–178°, 4-[(2-methyl-hydrazino)-methyl]-benzoic acid n-butylamide hydrobromide, m.p. 173°–175°, 4-[(2-methyl-hydrazino)-methyl]-benzoic acid sec.-butylamide hydrobromide, m.p. 155°–156°, 4-[(2-methyl-hydrazino)-methyl]-benzoic acid tert.-butylamide hydrobromide, m.p. 200°–201°, 4-[(2-methyl-hydrazino)-methyl]-benzoic acid isobutylamide hydrobromide, m.p. 177°–179°, 4-[(2-methyl-hydrazino)-methyl]-benzoic acid isopentylamide hydrobromide, m.p. 163°–164°, 4-[(2-methyl-hydrazino)-methyl]-benzoic acid n-pentylamide hydrobromide, m.p. 174–175°, 4-[(2-methyl-hydrazino)-methyl]-benzoic acid dimethylamide dihydrobromide, m.p. 142°–145°, 4-[(2-methyl-hydrazino)-methyl]-benzoic acid di-isopropylamide hydrobromide, m.p. 202°–203°, 4-[(2-methyl-hydrazino)-methyl]-benzoic acid pyrrolidine dihydrobromide hydrate, m.p. 139°–142°, 4-[(2-methyl-hydrazino)-methyl]-benzoic acid piperidine oxalate, m.p. 170°–172°, 4-[(2-methyl-hydrazino)-methyl]-benzoic acid allylamide hydrobromide, m.p. 158°–159°, 4[(2-methyl-hydrazino)-methyl]-benzoic acid (2-chloroethyl)amide hydrobromide, m.p. 168°–169°, 4[(2-methyl-hydrazino)-methyl]-benzoic acid (2-methylthioethyl)-amide hydrobromide, m.p. 152°–153°, 4-[(2-methyl-hydrazino)-methyl]-benzoic acid-(2-methylsulfonylethyl)-amide hydrobromide, m.p. 126°–128°.

EXAMPLE 4

16.5 g. of 4-[(2-methyl-1,2-dicarbobenzoxyhydrazino)methyl]-benzoyl chloride were added to 100 ml. of absolute benzene and treated with 3.1 g. of cyclopropylamine hydrochloride. 7.5 g. of triethylamine and 50 ml. of benzene were then dropped into the reaction mixture at 20°–30° with stirring. The reaction mixture was worked up as in Example 3, yielding 4-[(2-methyl-1,2-dicarbobenzoxy-hydrazino)-methyl]-benzoic acid cyclopropylamide, the carbobenzoxy groups of which were then removed by treatment with hydrogen bromide/glacial acetic acid. The product, 4-[(2-methyl-hydrazino)-methyl]-benzoic acid cyclopropylamide hydrobromide, melted at 180°–182°.

EXAMPLE 5

Reaction of 16.5 g. of 4-[(2-methyl-1,2-dicarbobenzoxyhydrazino)-methyl]-benzoyl chloride with morpholine according to the process of Example 3 above yielded the reaction product as a viscous yellow oil. The carbobenzoxy groups were split off by hydrogenolysis as follows:

the so-obtained 4-[(2-methyl-1,2-dicarbobenzoxyhydrazino)methyl]-benzoic acid morpholide was dissolved in 210 ml. of methanol and after the addition of 2.1 g. of 5% palladium-carbon, hydrogenated at room temperature and atmospheric pressure. After the hydrogen uptake had come to a standstill, the catalyst was filtered off, washed with methanol, and the filtrate concentrated in vacuo. The residue was taken up in 25 ml. of methanol, treated with a solution of 4.45 g. of oxalic acid in 20 ml. of methanol, and ether added thereto until the solution became turbid. Upon cooling, 4-[(2-methyl-hydrazino)-methyl]-benzoic acid morpholide oxalate crystallized out and after recrystallization from methanol/ether melted at 142°–144°.

By the same method and using 2-cyano-ethylamine, the following compound was prepared: 4-[(2-methyl-hydrazino)methyl]-benzoic acid (2-cyano-ethyl)-amide oxalate.

EXAMPLE 6

5.75 g. of sodium and then 79 g. of 1-methyl-1,2-dicarbobenzoxy-hydrazine were dissolved in 250 ml. of absolute alcohol. The solution was evaporated to dryness in vacuo at 40° and the residue dissolved in 150 ml. of dimethylformamide. Over 10 minutes, 46 g. of 4-chloromethyl-thioanisole were added to the solution, the temperature of the reaction mixture rising to 60°. The reaction mixture was then stirred for 2 hours at room temperature, poured into 1.5 liters of water and extracted with methylene chloride/ether. The extracts were washed several times with water, dried with sodium sulfate and concentrated in vacuo. The oily residue was dissolved in 400 ml. of glacial acetic acid and after the addition of 80 ml. of 30% hydrogen peroxide, heated on the steam bath for 2 hours. The reaction mixture was then evaporated to dryness in vacuo and the residue dissolved in 500 ml. of a 33% solution of hydrogen bromide in glacial acetic acid. After a short time, the product 1-methyl-2-(4-methylsulfonyl-benzyl)-hydrazine hydrobromide crystallized therefrom. It melted at 173°–175° (dec.).

EXAMPLE 7

10 g. of 4-[(2-methyl-1,2-dicarbobenzoxyhydrazino)-methyl]-benzoyl chloride were dissolved in a mixture of 50 ml. of benzene and 10 ml. of pyridine. While stirring, this solution was treated with 8 g. of 1-methyl-2-(4-amino-benzyl)-1,2-dicarbobenzoxyhydrazine in 30 ml. of benzene. After standing for one hour at room temperature, the reaction mixture was poured into water and extracted with methylene chloride. The methylene chloride extract was washed with sodium bicarbonate solution, dried with sodium sulfate and then concentrated. The residual viscous oil was decarbobenzoxylated with 70 ml. of a 33% solution of hydrogen bromide in glacial acetic acid. From this reaction mixture, the dihydrobromide of 4,4'-bis-[(2-methyl-hydrazino)-methyl]-benzanilide crystallized out. After recrystallization from methanol, it melted at 247°–248° (dec.).

EXAMPLE 8

By reaction of 23.4 g. of 4-[(2-methyl-1,2-dicarbobenzoxyhydrazino)-methyl]-benzoyl chloride with 4.85 g. of furfurylamine in a mixture of 8 ml. pyridine and 50 ml. of benzene according to the procedure of Example 4 above, followed by hydrogenolysis of the condensation product with palladium-carbon in methanol, there was obtained 4-[(2-methyl-hydrazino)-methyl]-benzoic acid furfurylamide, the oxalate of which melted at 170°–171° (dec.).

In an analogous manner, there was obtained 4-[(2-methylhydrazino)-methyl]-benzoic acid (3-methoxypropyl)-amide hydrochloride, m.p. 135°–136°.

By employing β-phenethylamine in the condensation step, and splitting off the carbobenzoxy groups with hydrogen bromide/glacial acetic acid, there was obtained 4-[(2-methyl-hydrazino)methyl]-benzoic acid phenethylamide hydrobromide, which, after recrystallization from ethanol/ether, melted at 180°–183°.

In an analogous manner, the following compounds were obtained by using the corresponding amines:
  4-[(2-methyl-hydrazino)-methyl]-benzoic acid (3-pyridyl methyl)-amide dihydrobromide, m.p. 136°–139°,
  4-[(2-methyl-hydrazino)-methyl]-benzoic acid benzylamide hydrobromide; m.p. 175°–177°.

EXAMPLE 9

23.4 g. of 4-[(2-methyl-1,4-dicarbobenzoxyhydrazino)methyl]-benzoyl chloride were dissolved in 60 ml. of benzene and, with stirring and cooling, added dropwise to a solution of 13.4 g. of 2-diethylaminoethylamine in 20 ml. of benzene. The mixture was permitted to stand overnight and then partitioned between a dilute solution of sodium hydroxide and ether. The ether phase was washed thoroughly neutral with water and then extracted with ¼ N hydrochloric acid. The hydrogen chloride extract was rendered strongly alkaline with sodium hydroxide, and then again extracted with ether. The ether solution was washed neutral with water, dried with sodium sulfate, and evaporated. The residual yellow oil was dissolved in 75 ml. of a 33% solution of hydrogen bromide in glacial acetic acid, and the resulting mixture permitted to stand for three hours at room temperature. It was then treated with ether, whereupon a hygroscopic salt separated out. This was separated and then dissolved in the minimum amount of water. The solution was then saturated with potassium carbonate and extracted with methylene chloride. The methylene chloride extracts were dried with potassium carbonate and concentrated. The residue was dissolved in methanol and treated with a methanolic solution of 2 equivalents of picric acid, whereupon the dipicrate of 4-[(2-methyl-hydrazino)-methyl]benzoic-benzoic acid diethylaminoethylamide crystallized out. It melted at 137°–139°.

In an analogous manner, then was obtained 4-[(2-methylhydrazino)-methyl]-benzoic acid dimethylaminoethylamide dihydrobromide, m.p. 131°–133°.

EXAMPLE 10

9 g. of ethanolamine were dissolved in a solution of 18.2 g. of sodium carbonate in 200 ml. of water. Over 2 hours, a solution of 65 g. of 4-[(2-methyl-1,2-dicarbobenzoxy-hydrazino)methyl]-benzoyl chloride in 150 ml. of ether was then added thereto dropwise with vigorous stirring at 0°–5°. The reaction mixture was then stirred overnight at 0°–5°. It was then extracted with a mixture of methylene chloride and ether, and the extract washed with water, 1 N hydrochloric acid, potassium bicarbonate solution and water, dried with sodium sulfate, and evaporated. The residual 4-[(2-methyl-1,2-dicarbobenzoxy-hydrazino)-methyl]benzoic acid (2-hydroxyethyl)-amide crystallized upon trituration with ether; m.p. 74°–76°. 68 g. thereof were dissolved in 210 ml. of a 33% solution of hydrogen bromide in glacial acetic acid, and the so-formed mixture permitted to stand at room temperature for 16 hours. The 4-[(2-methyl-hydrazino)-methyl]-benzoic acid (2-acetoxy-ethyl)-amide hydrobromide separated off; this hygroscopic salt melted at 119°–121° (dec.). It was then filtered off, washed with acetic acid/ether (4:1), washed with ether and dissolved in the minimum amount of water. This solution was saturated with potassium carbonate and extracted with ether. An etheric picric acid was then added to the ether extract, whereupon the picrate of 4-[(2-methyl-hydrazino)-methyl]-benzoic acid (2-acetoxy-ethyl)-amide crystallized out. After recrystallization from methanol, it melted at 143°–145°.

EXAMPLE 11

13.5 g. of diethanolamine were dissolved in a solution of 14.5 g. of sodium carbonate in 160 ml. of water. In the course of 2 hours, a solution of 52 g. of 4-[(2-methyl-1,2-dicarbobenzoxyhydrazin)-methyl]-benzoyl chloride in 150 ml. of ether was added thereto dropwise with vigorous stirring at 0°–5°. The mixture was then stirred overnight at 0°–5°. It was extracted with ethyl acetate and the ethyl acetate solution washed with sodium bicarbonate solution and sodium chloride solution; dried with sodium sulfate and evaporated. The residual viscous yellow oil was dissolved in 500 ml. of methanol and shaken with palladium-carbon in a hydrogen atmosphere until the carbobenzoxy groups had been hydrogenolyzed off. The catalyst was then filtered off, and the filtrate evaporated. The residue was dissolved in ethanol and treated with one equivalent of oxalic acid. Upon standing, the oxalate of 4-[(2-methyl-hydrazino)-methyl]-benzoic acid bis(2-hydroxyethyl)-amide crystallized out. It melted at 145°–146°.

EXAMPLE 12

106.5 g. of 4-[(2-methyl-1,2-dicarbobenzoxyhydrazino)methyl]-benzoyl chloride were dissolved in 400 ml. of diethyleneglycol dimethylether, and, with stirring in the course of 1½ hours at –75° to –68°, treated with a suspension of 70 g. of tritert.-butoxy-lithium-aluminum-hydride in 400 ml. of diethyleneglycol dimethylether. The temperature of reaction mixture was then allowed to rise to 0° in the course of 1 hour and then the mixture was treated with 60 ml. of water and 25.5 ml. of 3N sodium hydroxide. After a further 1½ hours, the reaction mixture was poured into a large amount of water, acidified with hydrochloric acid and the crude aldehyde taken up in ether. The ether solution was washed three times with 3N hydrochloric acid, two times with water, four times with sodium hydroxide solution and a further three times with water, dried with sodium sulfate and concentrated, yielding crude 4-[(2-methyl-1,2-dicarbobenzoxy-hydrazino)-methyl]benzaldehyde. In order to split off the carbobenzoxy groups, this product was dissolved in about 40 ml. of glacial acetic acid, and to this solution were added 280 ml. of a 33% solution of hydrogen bromide in glacial acetic acid. The reaction mixture was then permitted to stand for 3 hours at room temperature. The separated crystals were filtered off with suction, washed first with glacial acetic acid and then with absolute ether, and then dried in a dessicator over potassium hydroxide, yielding 4-[(2-methylhydrazino)-methyl]-benzaldehyde hydrobromide melting at 127°–132°.

EXAMPLE 13

52 g. of the product obtained in Example 8 by the condensation of 4-[(2-methyl-1,2-dicarbobenzoxyhydrazino)-methyl]-benzoyl chloride and furfuryl amine were hydrogenated in 300 ml. of ethanol in the presence of 6 g. of acetic acid and 1 g. of platinum until 2 equivalent amounts of hydrogen had been taken up. The catalyst was then filtered off and the solution concentrated, whereupon the residue was dissolved in 150 ml. of a 33% solution of hydrobromic acid in glacial acetic acid and allowed to stand for 3 hours. The crystallized product was filtered off, washed with glacial acetic acid and ether and recrystallized from a mixture of methanol, acetonitrile and ether, yielding 4-[(2-methyl-hydrazino)-methyl]-benzoic acid tetrahydrofurfuryl-amide dihydrobromide melting at 124°–125°.

EXAMPLE 14

23.8 g. of 4-[(2-methyl-1,2-dicarbobenzoxy-hydrazino)methyl]-benzoic acid (2-hydroxyethyl)-amide (obtained according to Example 10) were dissolved in 240 ml. of methanol and shaken in a hydrogen atmosphere together with 5 g. of palladium-carbon until the carbobenzoxy groups were hydrogenated off. The catalyst was then filtered off and the filtrates were concentrated. The residue was dissolved in 20 ml. of ethanol and treated with 1 equivalent of 25% alcoholic hydrochloric acid. On diluting with acetonitrile, the 4-[(2-methyl-hydrazino)-methyl]-benzoic acid (2-hydroxyethyl)-amide hydrochloride crystallized, which melted at 150°–152° after recrystallization from methanol/acetonitrile.

EXAMPLE 15

87.5 g. of 4-[(2-methyl-hydrazino)-methyl]-benzoic acid isopropylamide hydrobromide (obtained according to Example 3) were dissolved in 550 ml. of water. To this solution, there were added 1000 ml. of methylene chloride and, while cooling with ice and stirring under nitrogen atmosphere, 1200 g. of potassium carbonate portionwise. The methylene chloride layer was separated and the aqueous slurry extracted 3 times with 500 ml. of methylene chloride in a nitrogen atmosphere. The united methylene chloride extracts were concentrated in vacuo. The residue was dissolved under nitrogen in 100 ml. of methanol and treated, while cooling with ice, with 40 ml. of a 45% methanolic hydrochloric solution, which induces immediate crystallization. The crystals were filtered off and recrystallized from methanol, yielding 4-[(2-methyl-hydrazino)-methyl]-benzoic acid isopropylamide hydrochloride melting at 223°–226°.

EXAMPLE 16

A solution of 15.5 g. of 4-[(2-methyl-1,2-dicarbobenzoxyhydrazino)-methyl]-benzoyl chloride in 50 ml. of methylene chloride was poured, while stirring, into a solution of 2-(N-carbobenzoxy-methylamino)-ethylamine in 50 ml. of methylene chloride and 3.5 g. triethylamine. The mixture was stirred for 3 hours at room temperature and for 30 minutes at 40°, then poured onto water. The methylene chloride layer was separated and washed with 1N hydrochloric acid and with water. The methylene chloride solution was dried and concentrated and the residue dissolved in 75 ml. of a 33% solution of hydrobromic acid in glacial acetic acid and allowed to stand for 3 hours. The crystals formed were filtered off, washed with glacial acetic acid and ether, and recrystallized from ethanol, yielding 4-[(2-methylhydrazino)-methyl]-benzoic acid (2-methylaminoethyl)-amide dihydrobromide melting at 166°–168°.

The 2-(N-carbobenzoxy-methylamino)-ethylamine was prepared as follows:

20 g. of 2-methylamino-ethylamine in 100 ml. of absolute benzene was stirred with 28.7 g. of benzaldehyde. The mixture warmed up somewhat and became yellow. The benzene was evaporated in vacuo and the residue distilled under reduced pressure in a Hickmann-flask. After a little forerun, the desired fraction distilled at 106°–107°/13 mm. The N-benzylidene-N'-methylethylenediamine was obtained as a colorless oil of $n_D^{22} = 1.5452$ and a U.V.-absorption maximum at 245 m$\mu$. 25 g. of this product were dissolved in 150 ml. methylene chloride and thereto were added 16.5 g. of triethylamine and while stirring and cooling in an ice bath, 26.7 g. of carbobenzoxy chloride in 100 ml. of methylene chloride in such a way that the temperature did not rise over 20°. The mixture was stirred for 3 hours at room temperature and shaken with 100 ml. of water. The methylene chloride layer was washed three times with water and concentrated in vacuo. The yellow oil obtained was well mixed with 100 ml. of ether and 100 ml. of 6 N sulfuric acid for one hour at room temperature. The layers were separated, the aqueous layer extracted five times more with 30 ml. ether each time. To this ether extracts were added, while cooling on an ice bath, 50 g. of solid potassium hydroxide. The oily product was extracted with methylene chloride, the extract concentrated and the residue distilled under reduced pressure. The desired product distilled, after a short forerun, at 105°–112°/0.04 mm. as a colorless oil of $n_D^{24} = 1.5355$.

EXAMPLE 17

7.4 g. of methyl urea, 46.7 g. of 4-[(2-methyl-1,2-dicarbobenzoxy-hydrazino)-methyl]-benzoyl chloride, 8 g. of pyridine and 200 ml. of benzene were mixed and refluxed for 8 hours. After cooling down, the mixture was poured onto water and extracted with an ether/methylene chloride mixture. The extract was washed with water, with 1 N hydrochloric acid and again with water, dried over sodium sulfate and freed of the solvent by distillation. The residue crystallized upon triturating with methanol. The crystals were filtered off and dried, yielding 1-methyl-2-[4-(4-methyl-allophanoyl)-benzyl]-1,2-dicarbobenzoxy-hydrazine melting at 141°–142°. 25 g. thereof were dissolved in 50 ml. of glacial acetic acid and to it were added 100 ml. of a 33% solution of hydrobromic acid in glacial acetic acid. After 4 hours standing, the crystals formed were filtered off, washed with glacial acetic acid and ether, and recrystallized from methanol, yielding 1-methyl-2-[4-(4-methyl-allphanoyl)benzyl]-hydrazine hydrobromide of melting point 183°–183.5°.

In an analogous manner, the following products were obtained:
1-methyl-2-(4-allophanoyl-benzyl)-hydrazine hydrobromide, melting point 203°–204°,
1-methyl-2-[4-(4-ethyl-allophanoyl)-benzyl]-hydrazine hydrobromide, melting point 193°–194°,
1-methyl-2-[4-(4-butyl-allophanoyl)-benzyl]-hydrazine hydrobromide, melting point 171°–172°.

EXAMPLE 18

A suspension of 21.5 g. of sodium hydride in 80 ml. of dimethylformamide was added slowly, while stirring to a solution of 281 g. of 1-methyl-1,2-dicarbobenzoxyhydrazine in 300 ml. of dimethylformamide. After the evolution of hydrogen had subsided, there was added to the reaction mixture a solution of 167 g. of 4-(bromomethyl)-benzonitrile in 200 ml. of dimethylformamide and the mixture was then heated for 1 hour at 80°. The solvent was then almost completely distilled off in vacuo, the residue triturated with water and extracted with ether. The ether extract was washed with water, dried and concentrated. By recrystallization from dibutylether, there was obtained the 4-[(2-methyl-1,2-dicarbobenzoxy-hydrazino)-methyl]-benzonitrile melting at 68°.

43 g. of the above compound were mixed with 50 ml. of glacial acetic acid and 7.5 g. of tertiary butanol. Thereto were added dropwise, while stirring and cooling with ice to 0°–5° 5.6 ml. of concentrated sulfuric acid. The ice bath was then taken away and the mixture was stirred until homogeneous. It was then allowed to stand for 15 hours at room temperature, poured onto ice, extracted with ether and the ether extract was washed until neutral with water and 5% sodium carbonate solution. After drying over sodium sulfate, the ether was distilled off. The residue, 4-[(2-methyl-1,2-dicarbobenzoxy-hydrazino)-methyl]-benzoic acid tert.-butylamide, was dissolved in 150 ml. of a 35% solution of hydrogen bromide in glacial acetic acid and allowed to stand for 2 hours at room temperature. The crystallized salt that separated was filtered off and washed with glacial acetic acid/ether (4:1) and with ether. By recrystallization from methanol/acetonitrile/ether, there was obtained the 4-[(2-methyl-hydrazino)-methyl]benzoic acid tert.-butylamide hydrobromide melting at 200°–201°.

EXAMPLE 19

21.5 g. of 4-[(2-methyl-1,2-dicarbobenzoxy-hydrazino)methyl]-benzonitrile were dissolved in 70 ml. of a 33% solution of hydrogen bromide in glacial acetic acid, and allowed to stand for 20 hours at room temperature. The crystallized product was filtered off, washed with ether and recrystallized from alcohol, yielding 4-[(2-methyl-hydrazino)-methyl]-benzamide hydrochloride melting at 173°–175°.

EXAMPLE 20

15.8 g. of 4-[(2-methyl-1,2-dicarbobenzoxy-hydrazino)methyl]-benzoyl chloride were dissolved in 50 ml. of methylene chloride and, while stirring, added dropwise to a solution of 6.2 g. of 2-amino-1-butanol in 50 ml. of methylene chloride. Stirring was continued for 2 more hours at room temperature and 30 minutes at 40°, whereupon 50 ml. of water were added to the solution, which was then worked up according to Example 3. The yellowish glassy material obtained was dissolved in 200 ml. of methanol, shaken with 2 g. of 5% palladium-carbon in a hydrogen atmosphere, whereby ⅔ of the calculated amount of hydrogen had been absorbed after about 6 hours. The solution was then filtered and the filtrate concentrated in vacuo. The colorless residue was dissolved in 50 ml. of methanol and to it was added a solution of 3.2 g. of anhydrous oxalic acid in 25 ml. of methanol. Upon addition of some ether, a salt precipitated, which was recrystallized from ethanol/acetonitrile, yielding 4-[(2-methylhydrazino)-methyl]-benzoic acid (1-hydroxymethyl-propyl)-amide oxalate melting at 141°–143° (dec.).

EXAMPLE 21

15.8 g. of 4-[(2-methyl-1,2-dicarbobenzoxy-hydrazino)methyl]-benzoyl chloride were dissolved in 50 ml. of dry ether and, wherein 30 minutes within stirring, added dropwise to a solution of 3.3 g. of 2-amino-2-methyl-1-propanol and 3.6 g. of anhydrous sodium carbonate in 50 ml. of water. The solution was stirred overnight at 0°, the mixture diluted with 100 ml. of water and extracted 3 times with 100 ml. of methylene chloride each time. The united methylene chloride extracts were freed off the solvent in vacuo and the residue dissolved in 200 ml. of methanol, whereupon it was hydrogenated in the presence of 2 g. of 5% palladium-carbon. The colorless glacial material was transformed according to Example 20 into its oxalic acid salt. The crystalline crude material was recrystallized from methanol/acetonitrile, yielding 4-[(2-methyl-hydrazino)-methyl]-benzoic acid (1,1-dimethyl-2-hydroxy-ethyl)-amide oxalate as colorless platelets melting at 160°–162° (dec.).

EXAMPLE 22

The condensation product obtained in Example 21 from 4-[(2-methyl-1,2-dicarbobenzoxy-hydrazino)-methyl]-benzoyl chloride and 2-amino-2-methyl-1-propanol gave, upon treatment with hydrogen bromide in glacial acetic acid and subsequent precipitation with ether, an amorphous material that was dissolved in 50 ml. of water. To this solution were added 300 ml. of methylene chloride and, while cooling with ice under nitrogen, 150 g. of anhydrous potassium carbonate. The solution was well stirred, the organic phase decanted and the aqueous phase extracted three times with 300 ml. of methylene chloride each time. The united methylene chloride extracts were dried over potassium carbonate and the solvent was evaporated off. The residue was dissolved in 20 ml. of ethanol and to the mixture was immediately added a solution of 5 g. of anhydrous oxalic acid in 20 ml. of ethanol. Upon addition of a slight amount of ether the 4-[(2-methyl-hydrazino)methyl]-benzoic acid (1,1-dimethyl-2-acetoxy-ethyl)-amide oxalate formed colorless crystals melting at 116°–126° (dec.) after 2 recrystallizations from ethanol.

EXAMPLE 23

15.8 g. of 4-[(2-methyl-1,2-dicarbobenzoxy-hydrazino)methyl]-benzoyl chloride were dissolved in 50 ml. of methylene chloride. This solution was added, while stirring, dropwise to a suspension of 12.6 g. of 2-hydroxy-3,3,3-trichloro-propylamine in 150 ml. of methylene chloride. Stirring was continued for 2 hours at room temperature and 30 minutes at 40°, whereupon 50 ml. of water were added thereto. The product was worked up according to Example 3 and treated with hydrogen bromide in glacial acetic acid. The crystalline crude material was recrystallized from ethanol/acetonitrile/ether, yielding 4-[(2-methylhydrazino)-methyl]-benzoic acid [2-hydroxy-3,3,3-trichloropropyl]amide hydrobromide melting at 187°–189° (dec.).

EXAMPLE 24

6.4 g. of phosphorous pentachloride were suspended in 100 ml. of dry benzene. To this suspension was added, while stirring, a solution of 4-[(2-methyl-1,2-dicarbobenzoxy-hydrazino)-methyl]benzoic acid isopropylamide in 50 ml. of dry benzene. After 30 minutes, the solution became yellow and was concentrated in vacuo at 60°. The residue was treated with 1.8 g. of isopropylamine in 50 ml. of dry benzene and the mixture was heated to 60° for 2 hours. After evaporating off the solvent, there was obtained a yellow glacial material that was taken up in 80 ml. of a 33% solution of hydrogen bromide in glacial acetic acid. The product went into solution after short stirring, and after about 30 minutes crystallization began. After 1 hour standing at room temperature, the solid material was filtered off and recrystallized from glacial acetic acid yielding 1-methyl-2-[4-(N,N'-diisopropyl-amidino)-benzyl]-hydrazine dihydrobromide as slightly hydroscopic colorless prisms of melting point 128°–133° (dec.).

We claim:

1. A compound selected from the group consisting of compounds of the formula

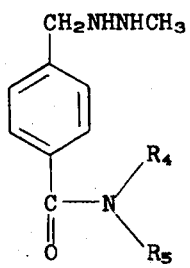

and pharmaceutically acceptable acid addition salts thereof; wherein $R_4$ is hydrogen and $R_5$ is selected from the group consisting of hydroxy-lower alkyl, (2-methylhydrazinomethyl)phenyl, hydrogen, lower alkoxy-lower alkyl, cyclo-lower alkyl, and cyano-lower alkyl.

2. A compound as in claim 1 which is 4-[(2-methylhydrazino)methyl]-benzamide.

3. A compound as in claim 1 which is 4-[(2-methylhydrazino)methyl]-benzoic acid (3-methoxypropyl)-amide.

4. A compound as in claim 1 which is 4-[(2-methylhydrazino)methyl]-benzoic acid (2-cyanoethyl)-amide.

5. A compound as in claim 1 which is 4-[(2-methylhydrazino)methyl]-benzoic acid cyclopropylamide.

6. A compound as in claim 1 which is 4,4'-bis-[(2-methylhydrazino)-methyl]-benzanilide.

7. A compound as in claim 1 of the formula

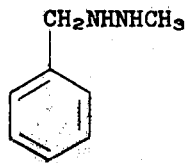

CONH-lower alkylene-OH

8. A compound as in claim 7 which is 4-[(2-methylhydrazino)methyl]-benzoic acid (2-hydroxyethyl)-amide.

* * * * *